United States Patent
Yamamoto et al.

(10) Patent No.: US 12,357,605 B2
(45) Date of Patent: Jul. 15, 2025

(54) MUSCLE BUILDING AGENT

(71) Applicant: KANEKA CORPORATION, Osaka (JP)

(72) Inventors: Ayumi Yamamoto, Takasago (JP); Shinichi Honda, Takasago (JP)

(73) Assignee: KANEKA CORPORATION, Osaka (JP)

( * ) Notice: Subject to any disclaimer, the term of this patent is extended or adjusted under 35 U.S.C. 154(b) by 933 days.

(21) Appl. No.: 17/440,379

(22) PCT Filed: Mar. 9, 2020

(86) PCT No.: PCT/JP2020/010058
§ 371 (c)(1),
(2) Date: Sep. 17, 2021

(87) PCT Pub. No.: WO2020/203079
PCT Pub. Date: Oct. 8, 2020

(65) Prior Publication Data
US 2022/0151987 A1 May 19, 2022

(30) Foreign Application Priority Data
Mar. 29, 2019 (JP) .................. 2019-067321

(51) Int. Cl.
*A61K 31/366* (2006.01)
*A23L 23/10* (2016.01)
*A61P 21/00* (2006.01)

(52) U.S. Cl.
CPC ............ *A61K 31/366* (2013.01); *A23L 23/10* (2016.08); *A61P 21/00* (2018.01)

(58) Field of Classification Search
None
See application file for complete search history.

(56) References Cited

U.S. PATENT DOCUMENTS

2004/0166181 A1* 8/2004 Hegenauer ........... A61K 36/185
514/184
2009/0281174 A1 11/2009 Ota et al.
(Continued)

FOREIGN PATENT DOCUMENTS

JP 2008-13473 A 1/2008
JP 2010-235542 A 10/2010
(Continued)

OTHER PUBLICATIONS

Bai et al., Journal of Agricultural and Food Chemistry 2008 56 (24), 11668-11674 (Year: 2008).*
(Continued)

*Primary Examiner* — Jeffrey S Lundgren
*Assistant Examiner* — Anthony Joseph Seitz
(74) *Attorney, Agent, or Firm* — Birch, Stewart, Kolasch & Birch, LLP

(57) ABSTRACT

Methods for building muscle tissue in a subject are described, which comprise administering an ellagitannin compound represented by the following formula (I) to a subject in need thereof:

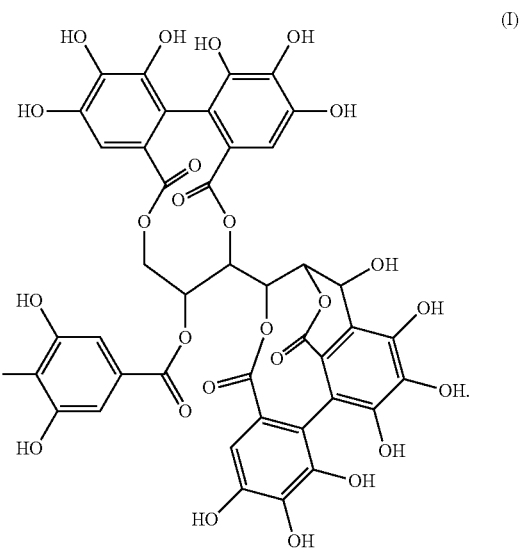

The ellagitannin compound represented by the formula (I) may be casuarinin or stachyurin, and is administered in a therapeutically effective amount. For instance, the ellagitannin compound may be administered in an amount effective for activating muscle satellite cells. These methods increase
(Continued)

and/or maintain muscle mass, as well as prevent and/or suppress a decrease of muscle mass and/or a decrease of muscle force. In certain embodiments, the subject is a human, such as an elderly person. In particular these methods are useful for subjects having or at risk of diseases such as sarcopenia, locomotive syndrome and/or frailty. The ellagitannin compound represented by the formula (I) may be administered as a component of a food or drink composition.

13 Claims, 4 Drawing Sheets

(56) References Cited

U.S. PATENT DOCUMENTS

| 2011/0224164 A1 | 9/2011 | Lebreton |
| 2012/0164243 A1 | 6/2012 | Rinsch et al. |
| 2014/0066401 A1 | 3/2014 | Lebreton |
| 2014/0073600 A1 | 3/2014 | Lebreton |
| 2016/0045413 A1 | 2/2016 | Lebreton |
| 2016/0213641 A1 | 7/2016 | Rinsch et al. |
| 2016/0213643 A1 | 7/2016 | Rinsch et al. |
| 2017/0143666 A1 | 5/2017 | Rinsch et al. |
| 2017/0143667 A1 | 5/2017 | Rinsch et al. |
| 2018/0303794 A1 | 10/2018 | Rinsch et al. |
| 2019/0070243 A1 | 3/2019 | Honda et al. |
| 2021/0059982 A1 | 3/2021 | Rinsch et al. |

FOREIGN PATENT DOCUMENTS

| JP | 2011-126834 A | 6/2011 |
| JP | 2012-77010 A | 4/2012 |
| JP | 2013-522283 A | 6/2013 |
| JP | 2014-501764 A | 1/2014 |
| WO | WO 2017/065077 A1 | 4/2017 |

OTHER PUBLICATIONS

Jasuja et al., 2012. Pharmacological Characterization and Beneficial Uses of Punica granatum. Asian Journal of Plant Sciences, 11: 251-267 (Year: 2012).*

Crozier et al., "Oral Leucine Administration Stimulates Protein Synthesis in Rat Skeletal Muscle," J. Nutr., vol. 136, No. 3, 2005, pp. 376-382.

Guo et al., "Anti-inflammatory potential of native Australian herbs polyphenols," Toxicology Reports, vol. 1, 2014, pp. 385-390.

International Search Report (PCT/ISA/210) issued in PCT/JP2020/010058, dated May 12, 2020.

* cited by examiner

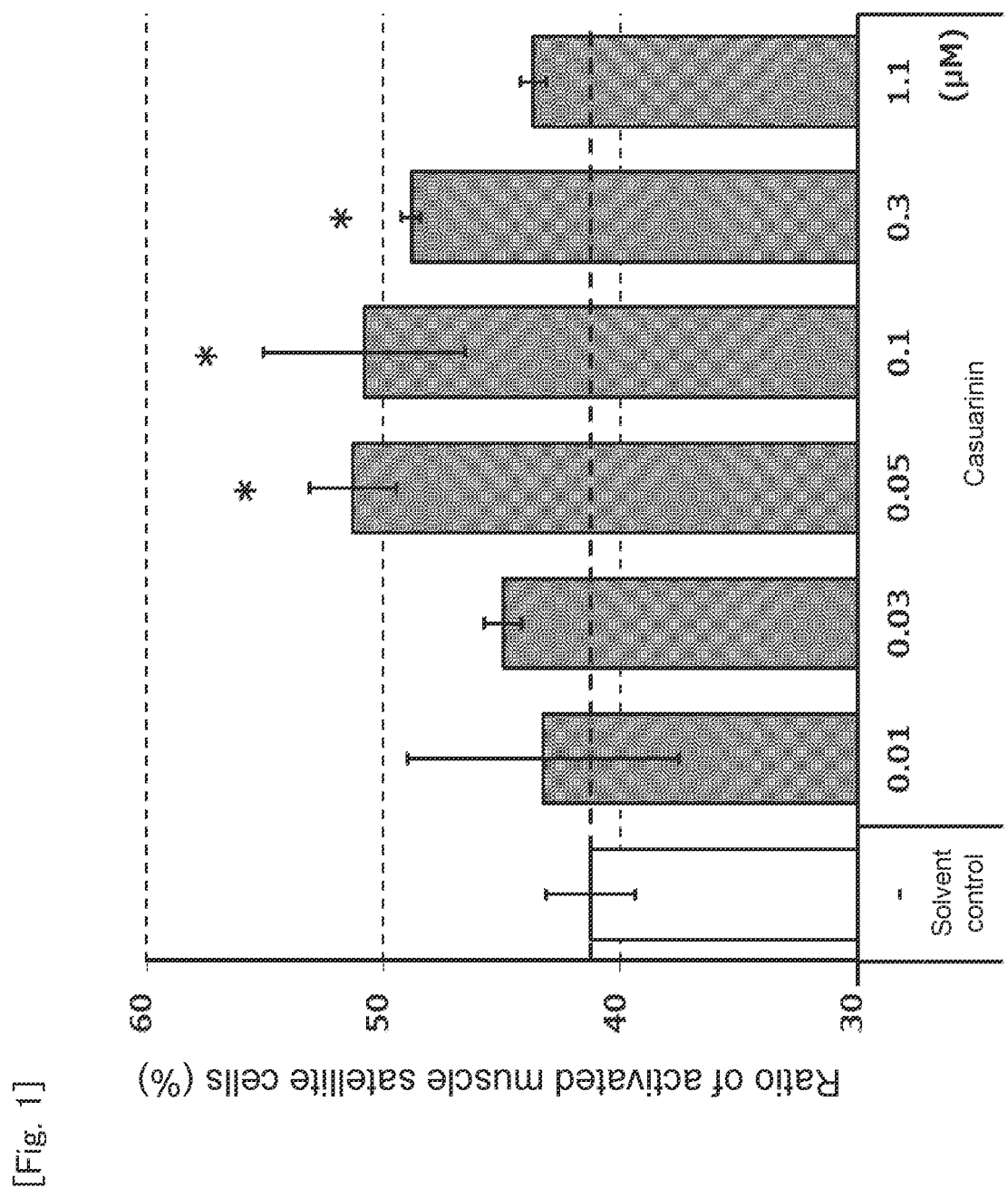
[Fig. 1]

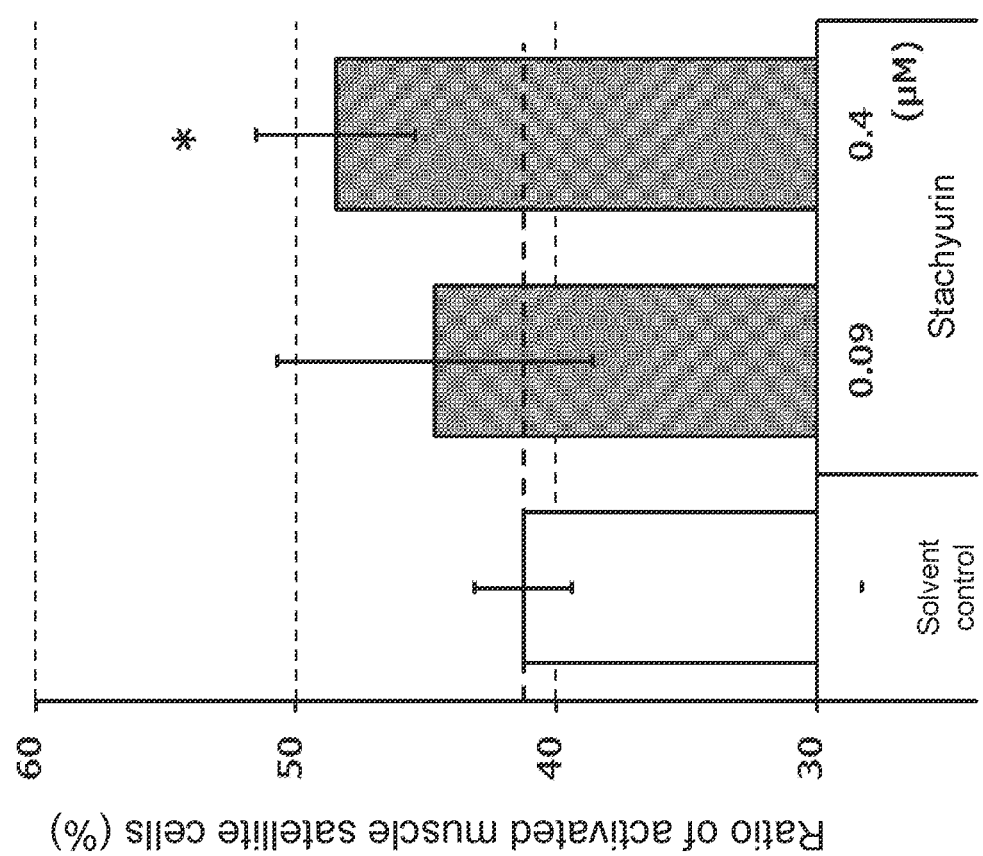
[Fig. 2]

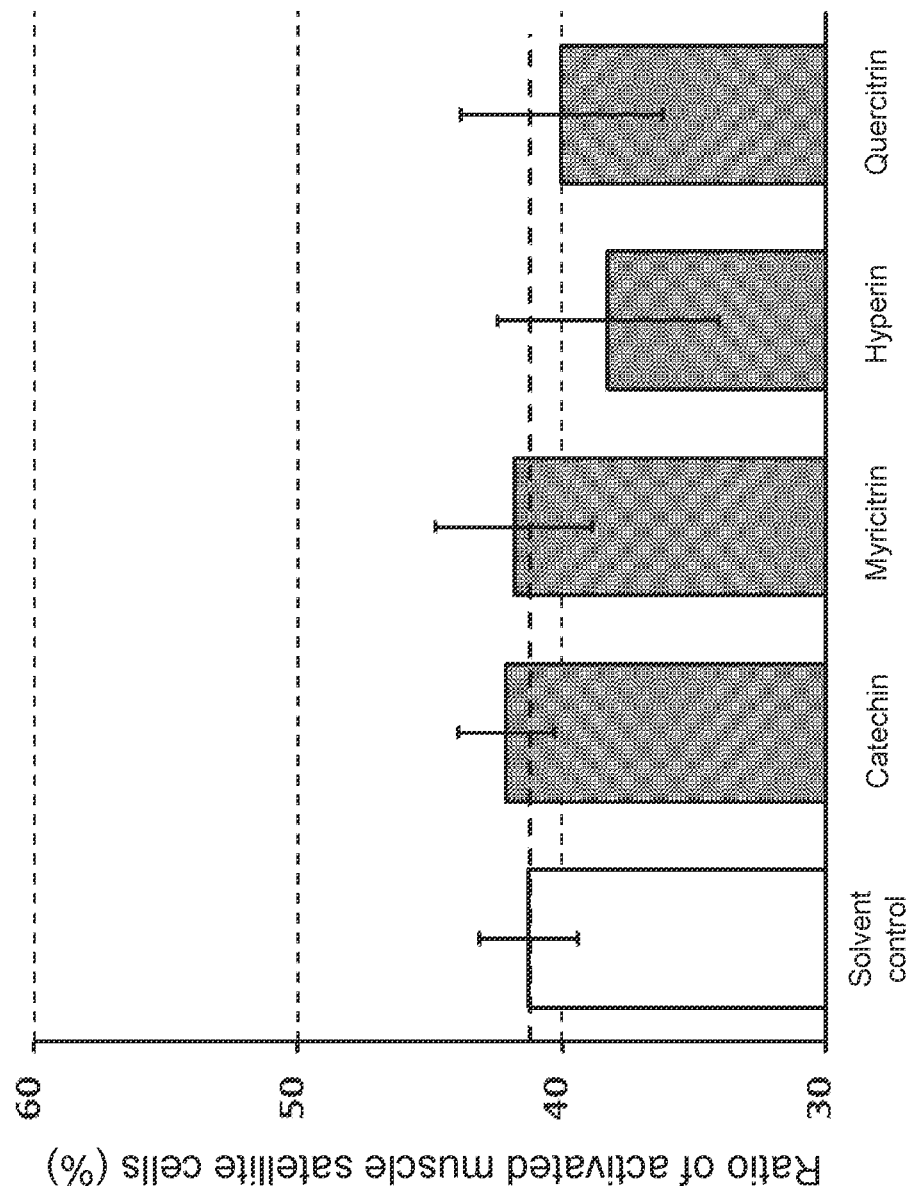
[Fig. 3]

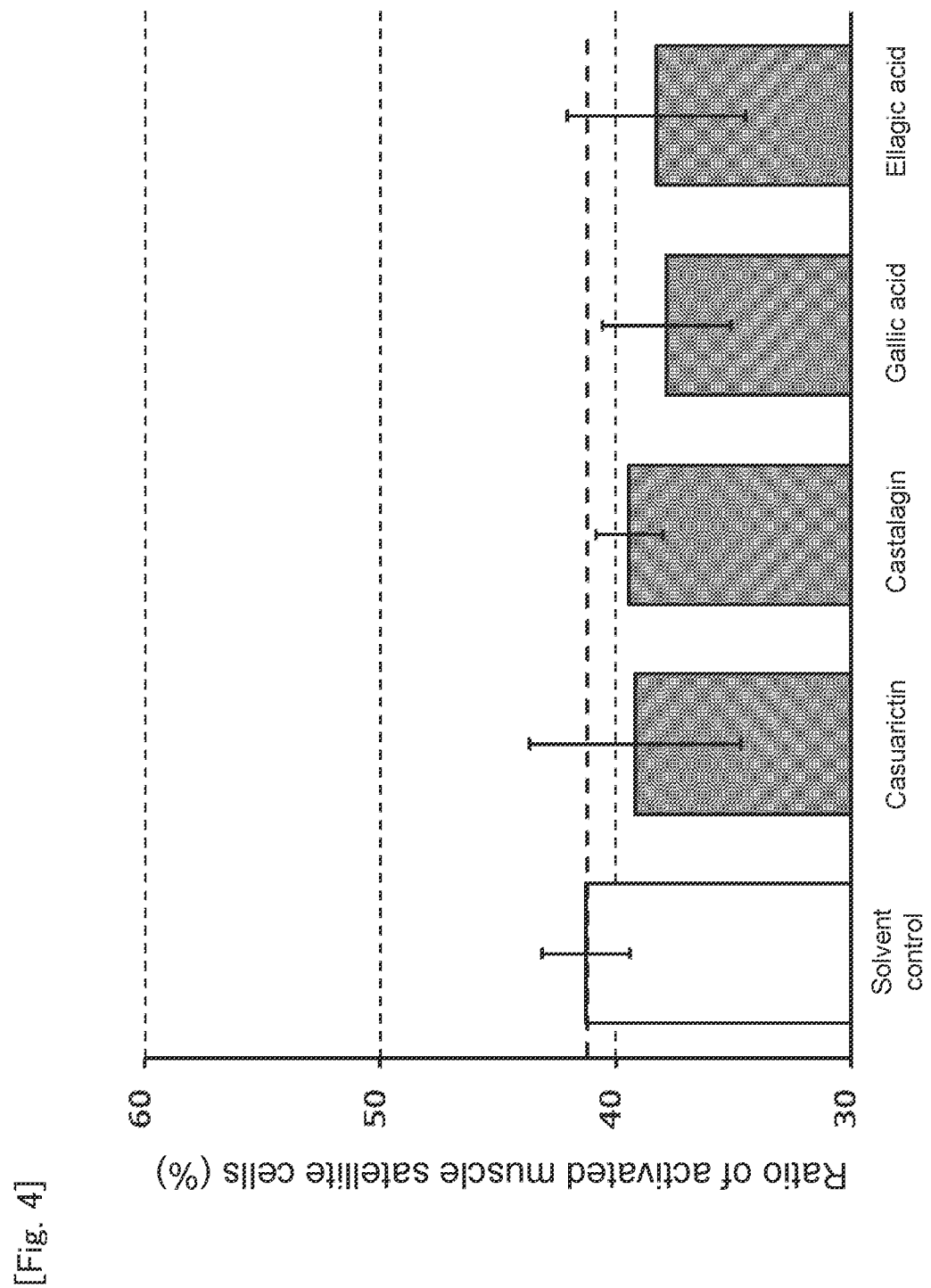
[Fig. 4]

MUSCLE BUILDING AGENT

TECHNICAL FIELD

The present invention relates to a muscle building agent by which muscle mass and/or muscle force can be increased or maintained or a decrease of muscle mass or a decrease of muscle force can be prevented or suppressed.

TECHNICAL FIELD

In recent years, muscle atrophy has become a major problem in association with acceleration of aging and insufficient exercise due to progress in transportation. Muscle atrophy means that muscle mass and muscle force are decreased. In general, it is said that muscle mass and muscle force are decreased from about 40 years old and many elderly people have sarcopenia. Sarcopenia mainly means a decrease in muscle mass and muscle force due to aging and is associated with locomotive syndrome and frailty, and it is pointed out that sarcopenia causes long-term care. Locomotive syndrome means a condition of decreased mobility function due to a disability of locomotive organs such as muscle, bone, joint, cartilage and intervertebral disc. Frailty means a condition in which physical and mental functions have declined. Thus, the decrease in muscle mass and muscle force lowers quality of life (QOL) and activities of daily living (ADL), and closely relates to the occurrence of complications and a greater burden.

Both of adequate nutritional intake and exercise are required to build muscle, that is, increase and maintenance of muscle mass and muscle force, as well as prevention and suppression of the decrease of muscle mass and muscle force. In case of elderly people, however, food intake tends to be decreased due to loss of appetite and an efficiency of converting ingested proteins and amino acids into muscle proteins is also decreased. In addition, it is not only difficult for elderly people with decreased physical strength and physical function to exercise continuously, but also an efficiency of muscle mass increase caused by exercise is decreased. Therefore, for example, when physical activity of elderly people decreases due to an injury or disease, muscle mass and muscle force further decrease, resulting in a negative cycle of further decline in physical activity and progression of muscle atrophy. Thus, elderly people have insufficient muscle gain caused by nutritional intake and exercise, so more effective means for building muscle is required.

Building muscle is required to maintain good health, improve exercise performance, prevent and alleviate obesity and metabolic syndrome, and slimming. Also, muscle enhancement is required for non-human animals to promote growth, increase meat and improve meat quality.

In order to build muscle, it is necessary to increase or maintain the size of muscle fibers constituting muscle. Muscle fibers are multinucleated cells, and the size of the cell is dependent on the number of the nuclei. Thus, it is necessary to increase the number of nuclei in order to increase or maintain muscle fibers. On the other hand, since the nuclei in muscle fibers do not increase, it is necessary to supply the nuclei to muscle fibers from the outside of the cells. The nuclei in muscle fibers are called myonuclei. The nuclei are supplied into the muscle fibers by muscle satellite cells, which locate between the basal membrane and the cell membrane of muscle fibers. Muscle satellite cells are normally in a "quiescent state" with a cell cycle arrest and in an undifferentiated state, but shift into an "activated state" with a cell cycle progression due to exercise, muscle damage and growth. Activated muscle satellite cells supply new nuclei into muscle fibers through processes such as proliferation, differentiation, and fusion with muscle fibers; as a result, muscle fibers are hypertrophied. Thus, activation of muscle satellite cells contributes to building muscle.

Growth hormone has been known as a component to build muscle. However, it is not preferred to intake a growth hormone continuously for a long period of time, since a growth hormone has problems of doping and side effects such as hypertension, carcinogenicity, liver damage, testicular atrophy, amenorrhea, delusion and paranoia.

Therefore, safe ingredients with muscle building effects have been searched. For example, Patent document 1 discloses a muscle function lowering inhibitor that contains catechins contained in a tea drink as an active ingredient. Patent document 2 discloses a muscle building agent that contains a plant of the genus Salacia of the family Celastraceae, which grows naturally in India, Sri Lanka and Southeast Asian countries, or an extract thereof. It is reported in Non-patent document 1 that leucine, which is a branched chain amino acid, has a muscle protein synthesis effect. Patent Document 3 discloses that an extract of pomegranate, punicalagin and ellagic acid contained in the extract, and metabolite thereof, "urolithin", activate mitochondria in skeletal muscle cells, and muscle mass increases by an administration of punicalagin, ellagic acid and urolithin. The effects on muscle are described in Patent documents 1 to 3, but there is no description of activation of muscle satellite cells in the Patent documents. Patent document 4 discloses a differentiation enhancing agent for satellite cells containing an apocynaceous plant Apocynum venetum or an extract therefrom as an active ingredient, but merely discloses a differentiation inducing effect on skeletal muscle cells and the ingredient does not activate muscle satellite cells. On the one hand, it is described in Patent document 5 that an extract of lemon myrtle has a muscle satellite cell activating effect.

PRIOR ART DOCUMENT

Patent Document

Patent document 1: JP 2008-13473 A
Patent document 2: JP 2010-235542 A
Patent document 3: JP 2014-501764 T
Patent document 4: JP 2012-77010 A
Patent document 5: WO 2017/065077

Non-Patent Document

Non-patent document 1: Crozier S J et al, J. Nutr., vol. 135, No. 3, 376-82, 2005

DISCLOSURE OF THE INVENTION

Problems to be Solved by the Invention

A decline in muscle mass and muscle force has become a serious problem with the progress of aging society, and the countermeasure is required in recent years as described above. Studies have been done to increase and maintain muscle mass and muscle force; however, only adequate nutrition intake and exercise are recommended as actual measures. Agents for preventing and suppressing a decline in muscle mass and muscle force are being distributed;

however, drugs and the like that are safe and that show a sufficient muscle building effect have not yet been distributed.

Therefore, the objective of the present invention is to provide a relatively safe muscle building agent by which muscle mass and muscle force can be effectively increased or maintained and by which a decrease of muscle mass and muscle force can be prevented or suppressed by activating muscle satellite cells.

Means for Solving the Problems

The inventors of the present invention repeated intensive studies in order to solve the above-described problems. As a result, the inventors completed the present invention by finding that the specific ellagitannin, which is a kind of polyphenol, activates muscle satellite cells, which plays an important role for an increase and a maintenance of muscle mass and muscle force.

The present invention is hereinafter described.

[1] A muscle building agent comprising an ellagitannin represented by the following formula (I) as an active ingredient.

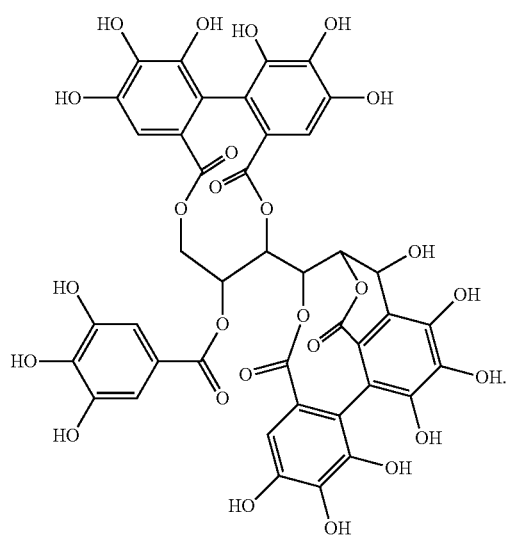

(I)

[2] The muscle building agent according to the above [1], wherein the ellagitannin represented by the formula (I) is casuarinin.
[3] The muscle building agent according to the above [1], wherein the ellagitannin represented by the formula (I) is stachyurin.
[4] The muscle building agent according to any one of the above [1] to [3], for increasing and/or maintaining muscle mass and/or muscle force or preventing and/or suppressing a decrease of muscle mass and/or a decrease of muscle force.
[5] The muscle building agent according to any one of the above [1] to [4], for administering 0.1 mg/kg weight/day or more of the ellagitannin represented by the formula (I).
[6] The muscle building agent according to any one of the above [1] to [5], wherein the muscle building agent is a food and drink composition.
[7] The muscle building agent according to the above [6], wherein the muscle building agent is a food with a functional claim.
[8] Use of an ellagitannin represented by the above formula (I) for building a muscle.
[9] The use according to the above [8], wherein the ellagitannin represented by the formula (I) is casuarinin.
[10] The use according to the above [8], wherein the ellagitannin represented by the formula (I) is stachyurin.
[11] The use according to any one of the above [8] to [10], for increasing and/or maintaining muscle mass and/or muscle force or preventing and/or suppressing a decrease of muscle mass and/or a decrease of muscle force.
[12] The use according to any one of the above [8] to [11], wherein the ellagitannin represented by the formula (I) is administered to a human.
[13] The use according to any one of the above [8] to [11], wherein the ellagitannin represented by the formula (I) is administered to a human or an elderly person with one or more diseases or having a potential of one or more diseases, and the disease is selected from the group consisting of sarcopenia, locomotive syndrome and frailty.
[14] The use according to any one of the above [8] to [13], wherein 0.1 mg/kg weight/day or more of the ellagitannin represented by the formula (I) is administered.
[15] The use according to any one of the above [8] to [14], wherein the ellagitannin represented by the formula (I) is administered as a component of a food and drink composition.
[16] A method for building a muscle, the method comprising the step of administering an ellagitannin represented by the above formula (I) as an active ingredient to a subject.
[17] The method for building muscle according to the above [16], wherein the ellagitannin represented by the formula (I) is casuarinin.
[18] The method for building muscle according to the above [16], wherein the ellagitannin represented by the formula (I) is stachyurin.
[19] The method for building muscle according to any one of the above [16] to [18], for increasing and/or maintaining muscle mass and/or muscle force or preventing and/or suppressing a decrease of muscle mass and/or a decrease of muscle force.
[20] The method for building muscle according to any one of the above [16] to [19], wherein the subject is a human.
[21] The method for building muscle according to any one of the above [16] to [19], wherein the subject is a human or an elderly person with one or more diseases or having a potential of one or more diseases, and the disease is one or more diseases selected from the group consisting of sarcopenia, locomotive syndrome and frailty.
[22] The method for building muscle according to any one of the above [16] to [21], wherein 0.1 mg/kg weight/day or more of the ellagitannin represented by the formula (I) is administered.
[23] The method for building muscle according to any one of the above [16] to [22], wherein the ellagitannin represented by the formula (I) is administered as a component of a food and drink composition.

[24] A method for building a muscle, the method comprising the step of administering the muscle building agent according to any one of the above [1] to [7].
[25] The method for building muscle according to the above [24], wherein a subject is a human or an elderly person with one or more diseases or having a potential of one or more diseases, and the disease is one or more diseases selected from the group consisting of sarcopenia, locomotive syndrome and frailty.
[26] A muscle satellite cell-activating agent comprising an ellagitannin represented by the above formula (I) as an active ingredient.
[27] The muscle satellite cell-activating agent according to the above [26], wherein the ellagitannin represented by the formula (I) is casuarinin.
[28] The muscle satellite cell-activating agent according to the above [26], wherein the ellagitannin represented by the formula (I) is stachyurin.
[29] The muscle satellite cell-activating agent according to any one of the above [26] to [28], for increasing and/or maintaining muscle mass and/or muscle force or preventing and/or suppressing a decrease of muscle mass and/or a decrease of muscle force.
[30] The muscle satellite cell-activating agent according to any one of the above [26] to [29], wherein 0.1 mg/kg weight/day or more of the ellagitannin represented by the formula (I) is administered.
[31] The muscle satellite cell-activating agent according to any one of the above [26] to [30], wherein the muscle satellite cell-activating agent is a food and drink composition.
[32] The muscle satellite cell-activating agent according to the above [31], wherein the muscle satellite cell-activating agent is a food with a functional claim.
[33] A method for activating a muscle satellite cell, the method comprising the step of administering an ellagitannin represented by the above formula (I) as an active ingredient to a subject.
[34] The method for activating muscle satellite cell according to the above [33], wherein the ellagitannin represented by the formula (I) is casuarinin.
[35] The method for activating muscle satellite cell according to the above [33], wherein the ellagitannin represented by the formula (I) is stachyurin.
[36] The method for building muscle according to any one of the above [33] to [35], for increasing and/or maintaining muscle mass and/or muscle force or preventing and/or suppressing a decrease of muscle mass and/or a decrease of muscle force.
[37] The method for activating muscle satellite cell according to any one of the above [33] to [36], wherein the subject is a human.
[38] The method for activating muscle satellite cell according to any one of the above [33] to [37], wherein the subject is a human or an elderly person with one or more diseases or having a potential of one or more diseases, and the disease is one or more diseases selected from the group consisting of sarcopenia, locomotive syndrome and frailty.
[39] The method for activating muscle satellite cell according to any one of the above [33] to [38], wherein 0.1 mg/kg weight/day or more of the ellagitannin represented by the formula (I) is administered.
[40] The method for activating muscle satellite cell according to any one of the above [33] to [39], wherein the ellagitannin represented by the formula (I) is administered as a component of a food and drink composition.

Effect of the Invention

The muscle building agent of the present invention is relatively safe, since the muscle building agent has the specific ellagitannin, which is a kind of polyphenol, an active ingredient. In addition, the muscle building agent has a function to activate muscle satellite cells similarly to exercise and can be used for increasing or maintaining muscle mass and muscle force and further preventing or suppressing a decrease of muscle mass and a decrease of muscle force.

BRIEF DESCRIPTION OF THE DRAWINGS

FIG. 1 is a graph to demonstrate the result of evaluation of a muscle satellite cell activating effect by casuarinin as an ellagitannin.

FIG. 2 is a graph to demonstrate the result of evaluation of a muscle satellite cell activating effect by stachyurin as ellagitannins.

FIG. 3 is a graph to demonstrate the result of evaluation of a muscle satellite cell activating effect by polyphenols other than an ellagitannin.

FIG. 4 is a graph to demonstrate the result of evaluation of a muscle satellite cell activating effect by ellagitannins other than casuarinin and stachyurin, and by partial structures of casuarinin and stachyurin.

MODE FOR CARRYING OUT THE INVENTION

The muscle building agent of the present invention comprises the ellagitannin represented by the formula (I). The ellagitannin represented by the formula (I) is hereinafter described as "ellagitannin (I)". The muscle building agent of the present invention has a muscle building function.

The term "muscle building" in the present invention means that not only muscle mass or muscle force is increased or maintained but also a decline of muscle mass or a decline of muscle force is prevented or suppressed. Thus, the "muscle building agent" of the present invention can be used for increasing or maintaining muscle mass and muscle force and further preventing or suppressing a decline of muscle mass and muscle force. The term "muscle mass" means a weight of a muscle, and the term "muscle force" means a force that muscle exerts by contracting. Since the muscle building agent of the present invention has an effect of activating muscle satellite cells, when the muscle building agent according to the present invention is ingested, muscle satellite cells proliferate and differentiate, and fuse into muscle fibers to create new myonuclei. As a result, muscle mass increases. In other words, the muscle building agent increases the number of muscle satellite cells and is also an agent for activating a muscle satellite cell. The muscle building agent of the present invention can be used for building muscle of a healthy people and an athlete who need to build muscle and a child and a younger people who need physical development such as an increase of weight. In addition, the muscle building agent of the present invention can be used for preventing or relieving a decline in muscle mass and muscle force caused by an inaction due to insufficient exercise, long-term laid down condition and plaster cast, malnutrition, sarcopenia or the like; a secondary sarcopenia due to malnutrition, invasion, cachexia or the like; a myopathy such as muscular dystrophy and congenital myopathy; and a neurogenic disease such as amyotrophic lateral sclerosis and spinal muscular atrophy. Furthermore, the muscle building agent of the present invention can be used for preventing or relieving a condition and disease due to a decline in muscle mass and muscle force, such as locomotive syndrome and frailty. In other words, the muscle building agent of the present invention can be used for maintaining or building muscle mass and muscle force of a human whose muscle mass and muscle force are decreased, such as an elderly person. An elderly person means, for example, a 60-year-old or older person and more preferably a 70-year-old or older person. Also, the muscle building agent of the present invention can be used for an animal such as a domestic animal of which growth promotion, an increase in meat amount and an improvement in meat quality are required. The muscle building agent of the present invention can be also used for preventing or relieving obesity and metabolic syndrome, and for slimming, since a muscle can be built by the muscle building agent of the present invention.

Muscle satellite cells are undifferentiated muscle stem cells that exist between basal membrane and cell membrane of muscle fibers. The term "activation of a muscle satellite cell" in the present invention means that a muscle satellite cell undergoes transition from a quiescent state to growth phase and supplies a nucleus into a muscle fiber through processes of differentiation and fusion with the muscle fiber. The activation of muscle satellite cells causes muscle fibers to enlarge and finally builds muscle, since the number of nuclei that relates to a size of muscle fibers is increased by the activation of muscle satellite cells. A degree of the activation of muscle satellite cells can be evaluated by measuring the number of the cell, the amount of nucleic acid and the amount of incorporated DNA analog such as bromodeoxyuridine.

An ellagitannin is a type of polyphenols widely existing in the plant, such as oak. An ellagitannin is a compound group having a structure formed by an ester bond between polyols such as glucose and polyphenolic acids such as hexahydroxydiphenic acid and gallic acid. In an ellagitannin, the hexahydroxydiphenic acid moiety is referred to as a hexahydroxydiphenoyl group, and the gallic acid moiety is referred to as a galloyl group. An ellagitannin is a highly stable compound but is hydrolyzed by acids, alkalis and enzymes. The hexahydroxydiphenic acid separated from the ellagitannin by hydrolysis is rapidly subjected to an intramolecular dehydration condensation as the following formula to become stable ellagic acid. Many plants containing ellagitannins are used as crude drugs, and the ellagitannins having a physiological activity such as antioxidant effect and anticancer effect are known.

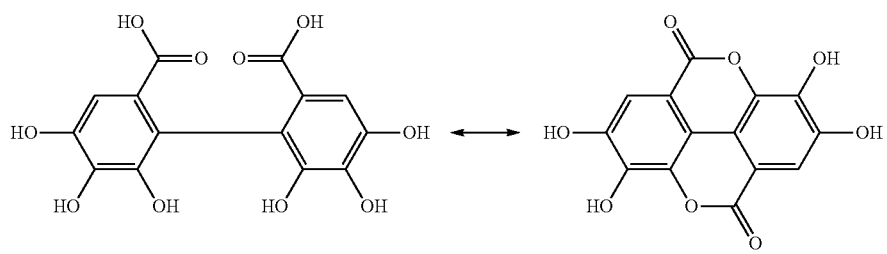 [SMILES: O=C(O)c1cc(O)c(O)c(O)c1-c1c(C(=O)O)cc(O)c(O)c1O ; O=c1oc2c(O)c(O)cc3c(=O)oc4c(O)c(O)cc1c4c23]

The ellagitannin (I) is a compound formed by ester bonds between glucose and two hexahydroxydiphenoyl groups and between glucose and one galloyl group. The glucose in the ellagitannin (I) has an open-formed structure, and two hexahydroxydiphenoyl groups are respectively ester-bonded to the hydroxy groups at the $2^{nd}$ and the $3^{rd}$ positions and the hydroxy groups at the $4^{th}$ and the $6^{th}$ positions of the glucose, and a galloyl group is ester-bonded to the hydroxy group at the $5^{th}$ position. In addition, the carbon atom at the $1^{st}$ position of the glucose is an anomeric carbon atom and forms a C-glycosidic bond with the hexahydroxydiphenoyl group linked to the $2^{nd}$ and the $3^{rd}$ positions. An example of the ellagitannin (I) includes casuarinin and stachyurin. Casuarinin and stachyurin are different molecular configuration at the $1^{st}$ position of the glucose, and casuarinin has an α-glucose structure and stachyurin has a β-glucose structure.

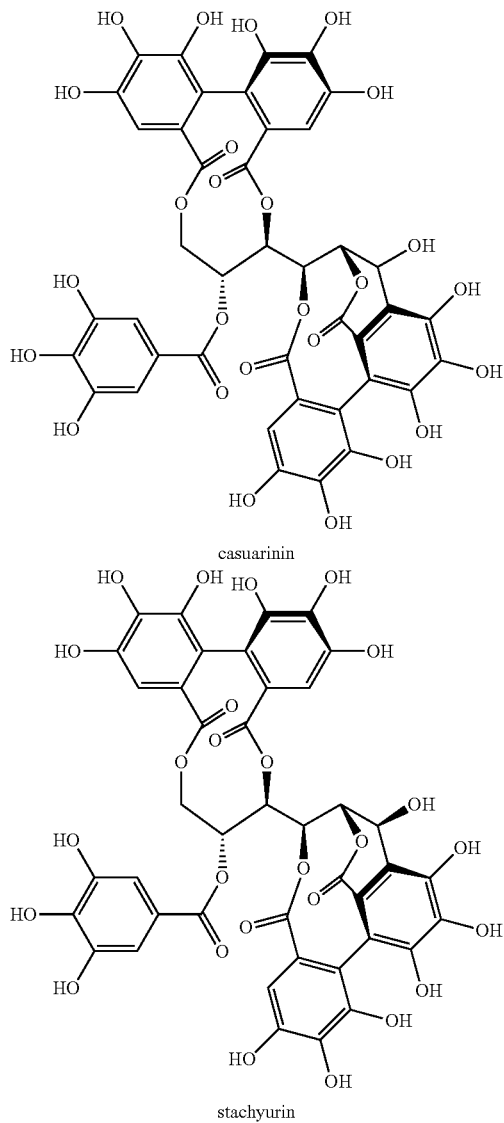

casuarinin stachyurin

A method for obtaining the ellagitannin (I) is not particularly restricted, and the ellagitannin (I) can be chemically synthesized from a publicly known compound. Alternatively, the ellagitannin (I) can be purified from a plant. For example, casuarinin and/or stachyurin is contained in Casu- arinaceae *Casuarina stricta*; Stachyuraceae *Stachyurus praecox*; Myrtaceae *Psidium guajava* and *Psidium cattleianum*; Myrtaceae *Syzygium jambos*, *Syzygium samarangense* and *Syzygium aqueum*; Myrtaceae *Feijoa sellowiana*; Myrtaceae *Eucalyptus viminalis*; and Myrtaceae *Pimenta dioica*. In addition, the present inventors uniquely found that casuarinin and stachyurin are contained in lemon myrtle, i.e. *Backhousia citriodora*, as a Myrtaceae *Backhousia* plant.

A method for purifying the ellagitannin (I) from a plant is not particularly restricted. Since the ellagitannin (I) is water-soluble due to many hydroxy groups, the ellagitannin (I) can be extracted from a part of a plant containing the ellagitannin (I), such as leaf, stem, root, branch and flower, using an aqueous solvent such as water, a water-soluble organic solvent and a mixed solvent thereof. The target ellagitannin (I) may be further purified from the obtained extract liquid directly or after the extract liquid is dried by drying under reduced pressure, lyophilization, drum drying, spray drying or the like.

The ellagitannin (I) may form a salt in the muscle building agent, and the muscle building agent containing such a salt of the ellagitannin (I) is included in the technical scope of the present invention. An example of the salt includes a sodium salt and a potassium salt.

A dosage form of the muscle building agent according to the present invention is not particularly restricted and for example, may be the ellagitannin (I) itself, a composition containing other component, or a solution or a suspension thereof. In addition, a plant containing the ellagitannin (I) and a fraction extracted or purified from the plant may be used as the active ingredient of the present invention. A dosage form of the muscle building agent is not particularly restricted and is exemplified by tablet, powder, capsule, sugar-coated tablet, granule, liquid and external preparation.

A pharmaceutically acceptable additive may be mixed in the muscle building agent of the present invention depending on a dosage form. Such an additive is exemplified by an excipient, disintegrating agent, lubricant, binder, antioxidant, coloring agent, sweetener, anticoagulant, a dissolution aid for the active ingredient, and stabilizer. The excipient is not particularly restricted, and exemplified by white sugar, lactose, glucose, corn starch, dextrin, mannitol, crystalline cellulose, calcium phosphate, calcium sulfate and magnesium sulfate. The disintegrating agent is not particularly restricted, and exemplified by starch, agar, calcium citrate, calcium carbonate, sodium hydrogencarbonate, dextrin, crystalline cellulose, carboxymethylcellulose and tragacanth. The lubricant is not particularly restricted, and exemplified by talc, magnesium stearate, polyethylene glycol, silica and hydrogenated vegetable oil. The binder is not particularly restricted, and exemplified by ethyl cellulose, methyl cellulose, hydroxypropyl methylcellulose, tragacanth, shellac, gelatin, gum arabic, polyvinylpyrrolidone, polyvinyl alcohol, polyacrylic acid, polymethacrylic acid and sorbitol. The antioxidant is not particularly restricted, and exemplified by ascorbic acid, tocopherol, sodium hydrogen sulfite, sodium thiosulfate, sodium pyrosulfite and citric acid. The coloring agent is not particularly restricted, and exemplified by a coloring agent that is allowed to be added to a medicinal product or a food. The sweetener is not particularly restricted, and exemplified by a sweetener that is allowed to be added to a medicinal product or a food. The anticoagulant is not particularly restricted, and exemplified by stearic acid, talc, light anhydrous silicic acid and hydrous silicon dioxide. The dissolution aid for the active ingredient is not particularly restricted, and exemplified by an organic acid such as fumaric acid, succinic acid and malic acid. The stabilizer is not particularly restricted, and exemplified by benzoic acid, sodium benzoate, ethyl parahydroxybenzoate and propylene glycol.

The muscle building agent of the present invention can be used as, for example, a food and drink composition, a medicinal product, a quasi-drug, a feed, a pet food or a drug for animal.

The muscle building agent of the present invention may be directly used or administered as a food and drink composition having a muscle building action, such as a food for specified health use and a food with a functional claim, medicinal product, quasi-drug, supplement, feed, pet food or drug for animal, and may be contained in a food and drink composition, medicinal product, quasi-drug, feed, pet food or drug for animal to be used. Also, the muscle building agent of the present invention may be in a form of an oral intake preparation. An oral intake preparation has a form that can be orally administered, such as a capsule, tablet, powder, chewable preparation, syrup and solution. An example of a capsule includes a hard capsule, microcapsule and soft capsule. A base material of a capsule is not particularly restricted, and is exemplified by an agent usable as a food additive for the production in addition to gelatin derived from cattle bone, cow skin, pig skin or fish skin. An example of the agent for the production includes carrageenan and alginic acid derived from seaweed; locust bean gum and guar gum derived from a plant seed; pullulan and curdlan derived from a microorganism; and cellulose.

The muscle building agent of the present invention can be added in a general food and drink. A food and drink in which the muscle building agent of the present invention is contained is not particularly restricted, and is exemplified by a drink such as milk drink, soft drink, sports drink, nutritional drink, cosmetic drink and liquid nutrient; a sweet stuff such as chewing gum, chocolate, candy, jelly, cake, biscuit and cracker; a frozen dessert such as ice cream; a noodle such as wheat noodle, Chinese noodle, spaghetti and instant noodle; a fish paste cake such as a semicircle-shaped fish paste cake, tube-shaped fish paste cake and boiled flat fish cake; a seasoning such as dressing, mayonnaise and sauce; bread, ham, rice cooker, rice, soup, various retort foods and various frozen foods. The food and drink containing the muscle building agent of the present invention can be used as a health food, supplement, functional food, food with function claim, dietary supplement, food for specified health use, nutrient function food, nursing care food, smile care diet, chewing/swallowing assisting food, concentrated liquid food and food for sick people. It goes without saying that the muscle building agent of the present invention can be used in other food form and in a pet food and livestock feed.

A form of the muscle building agent of the present invention may be a parenteral preparation. For example, the muscle building agent may be applied to a skin. In such a case, the dosage form is not particularly restricted, and is exemplified by cream, paste, jelly, gel, emulsion and liquid prepared by dissolving or mixing and dispersing the muscle building agent of the present invention in a base material, such as ointment, liniment, lotion and spray; a preparation such as poultice, prepared by dissolving or mixing and dispersing the ellagitannin (I) in a base material and applying the obtained solution or dispersion on a support substrate; a preparation such as plaster and tape, prepared by dissolving or mixing and dispersing the above-described composition in an adhesive agent and applying the obtained adhesive agent on a support substrate.

When the muscle building agent of the present invention is used as a quasi-drug, and such a quasi-drug is defined in the pharmaceutical affairs law and is exemplified by an oral preparation. Such an oral preparation is exemplified by a liquid preparation such as extract, elixir, syrup, tincture and limonade, and a solid preparation such as capsule, granule, pill, powder and tablet.

The muscle building agent of the present invention comprises the ellagitannin represented by the formula (I) as an active ingredient. A ratio of the ellagitannin in the muscle building agent is dependent on a dosage form or the like and may be adjusted to, for example, 0.0001 mass % or more. The ratio is preferably 0.001 mass % or more or 0.003 mass % or more, more preferably 0.01 mass % or more or 0.03 mass % or more, and even more preferably 0.1 mass % or more or 0.3 mass % or more. The upper limit of the ratio may be 100 mass %, and the ratio is preferably 50 mass % or less or 40 mass % or less, more preferably 20 mass % or less or 10 mass % or less, and even more preferably 7 mass % or less or 5 mass % or less.

The muscle building agent of the present invention exhibits an excellent muscle building effect, such as an ability to activate muscle satellite cells. The muscle satellite cells activation effect can be evaluated by, for example, the following in vitro test. Specifically, muscle satellite cells are isolated from an animal and cultured in a culture medium containing test sample for 24 hours. Then, bromodeoxyuridine (BrdU) is added thereto at the final concentration of 10 µM, and the mixture is incubated for 2 hours. Next, the muscle satellite cells are fixed at 4° C. for 10 minutes with ice-cooled methanol containing 0.1% $H_2O_2$ and are subjected to DNA denaturation treatment at 37° C. for 1 hour using 2 N hydrochloric acid, and BrdU positive cells are detected by using anti-BrdU antibody as a primary antibody, HRP-conjugated anti-mouse IgG antibody as a secondary antibody, and coloring with diaminobenzidine (DAB). The ratio of BrdU positive cells to the total number of cells is calculated as the ratio of activated muscle satellite cells. It is judged with respect to the ratio of activated muscle satellite cells of the muscle building agent according to the present invention that muscle satellite cells are activated in the case where a ratio of activated muscle satellite cells is increased by a treatment with a test substrate in comparison with a solvent control. An increase to a solvent control is preferably 2% or more, more preferably 3% or more and even more preferably 5% or more.

A method for building muscle according to the present invention comprises the step of administering the muscle building agent of the present invention. A subject to whom the muscle building agent of the present invention is administered is exemplified by a subject whose muscle mass and muscle force should be increased and a subject whose muscle mass and muscle force should be prevented from being decreased. A specific example of the subject to whom the muscle building agent is administered includes a human or an elderly person with one or more diseases or having a potential of one or more diseases selected from the group consisting of sarcopenia, locomotive syndrome and frailty.

The muscle building agent of the present invention can be administered to an animal other than a human in addition to a human. Accordingly, the present invention relates to a method for building muscle, characterized in comprising the step of administering the muscle building agent of the present invention to an animal. A subject animal to which the muscle building agent is administered is exemplified by cultured animal, companion animal and competitive animal. A cultured animal is not particularly restricted and is exemplified by a domestic animal such as horse, cow, pig, sheep, goat, camel and llama; an experimental animal such as mouse, rat, guinea pig and rabbit; a poultry such as chicken, duck, turkey and ostrich; a fish; a crustacean; and a shellfish. A companion animal is not particularly restricted and is exemplified by dog and cat. A competitive animal is not particularly restricted and is exemplified by racehorse.

An administration frequency and dosage amount of the muscle building agent of the present invention may be appropriately adjusted depending on a subject to be administered, age, sex, condition and the like, and an amount capable of exerting a muscle building effect is administered to a subject to be administered. For example, the lower limit of the dosage amount to be administered to a human per one day is not particularly restricted, and a dosage amount of the ellagitannin (I) per one day is preferably 0.1 mg/kg weight or more or 0.5 mg/kg weight or more, more preferably 1 mg/kg weight or more or 2 mg/kg weight or more, and even more preferably 5 mg/kg weight or more. The upper limit of the dosage amount to be administered to a human per one day is not also particularly restricted, and a dosage amount of the ellagitannin (I) per one day is preferably 1000 mg/kg weight or less, more preferably 500 mg/kg weight or less, and even more preferably 100 mg/kg weight or less. A frequency of administration per one day is not particularly restricted, and the muscle building agent may be administered in a single dose or in several doses within a desired administration range.

The muscle building agent of the present invention can be appropriately used in combination with exercise such as resistance exercise, physical therapy, rehabilitation and the like for the purpose of improving the effect of increasing or maintaining muscle mass and muscle force. Also, the muscle building agent of the present invention can be used in combination with other medicine or food having a muscle building action for the purpose of improving the effect of increasing or maintaining muscle mass and muscle force. A food having a muscle building action is not particularly restricted, and is exemplified by whey protein, whey peptide, casein, casein peptide, soybean protein, soybean peptide, wheat protein, wheat peptide, an amino acid such as valine, leucine, isoleucine, arginine, citrulline and ornithine, creatine, and β-hydroxy-β-methybutyric acid.

The present application claims the benefit of the priority date of Japanese patent application No. 2019-67321 filed on Mar. 29, 2019. All of the contents of the Japanese patent application No. 2019-67321 filed on Mar. 29, 2019, are incorporated by reference herein.

EXAMPLES

The present invention is hereinafter described in more detail with Examples. The present invention is, however, not restricted to the following Examples in any way, and it is possible to work the present invention according to the Examples with an additional appropriate change within the range of the above descriptions and the following descriptions. Such a changed embodiment is also included in the technical scope of the present invention.

Example 1: Preparation of Casuarinin

Dried leaves (100 g) of lemon myrtle (*Backhousia citriodora*), a *Myrtaceae* family plant, were added in water (500 mL), and the mixture was stirred at 50° C. for 2 hours for extraction. The solid components were separated by filtration to obtain a liquid extract. The obtained liquid extract was concentrated under reduced pressure and lyophilized to remove the solvent and to obtain a lemon myrtle extract (16.1 g). The obtained extract (120 mg) was dissolved in water (1 mL) and fractionated by high-performance liquid chromatography (HPLC) in the following condition. Casuarinin (40 mg) was obtained by repeating fractionation. The structure of the compound was confirmed by NMR analysis and mass spectrometry.

HPLC Condition
    Column: "YMC-Pack ODS-A" manufactured by YMC, φ10 mm×150 mm
    Eluent: gradient of a mixture of acetonitrile—methanol and 0.1% formic acid aqueous solution Example 2: Preparation of Stachyurin Stachyurin was prepared from lemon myrtle similarly to Example 1.

Example 3: Evaluation of Muscle Satellite Cell Activating Effect (1) Isolation of Muscle Satellite Cells Muscle tissues were isolated from the upper hindlimb and back of 6-month old male SD rat (from Japan SLC). The muscle tissues were trimmed of adipose and connective tissue, minced, and treated with PBS containing 1.25 mg/mL protease (Sigma) at 37° C. for 1 hour. After muscle fiber fragments and tissue debris were removed by centrifugation, the cells were seeded on plates coated with polylysine (Sigma) and fibronectin (Sigma). After the cells were cultured in 5% $CO_2$ atmosphere at 37° C. for 24 hours, muscle satellite cells were isolated by washing with PBS. DMEM ("Dulbecco's Modified Eagle Medium", Thermo Fisher Scientific) containing 10% horse serum (Thermo Fisher Scientific) was used as a culture media. The culture media is hereinafter abbreviated as "10% HS-DMEM".

(2) Treatment with Casuarinin or Stachyurin

The casuarinin prepared in Example 1 or the stachyurin prepared in Example 2 was dissolved in water and added in 10% HS-DMEM to prepare the 10% HS-DMEM containing casuarinin or stachyurin. The culture medium of the isolated muscle satellite cells were exchanged for the 10% HS-DMEM containing casuarinin or stachyurin, and the muscle satellite cells were cultured for 24 hours. Casuarinin concentrations were adjusted to 0.01 to 1.1 μM (13 to 1000 ng/mL), and stachyurin concentrations were adjusted to 0.09 to 0.4 μM (83 to 333 ng/mL). As a solvent control, 10% HS-DMEM was used.

(3) Evaluation of Muscle Satellite Cell Activating Effect

Bromodeoxyuridine (BrdU, Sigma) was added to the culture medium at the final concentration of 10 μM, and the mixture was incubated for 2 hours. Then, the muscle satellite cells were fixed at 4° C. for 10 minutes with ice-cooled methanol containing 0.1% $H_2O_2$ and were further subjected to DNA denaturation treatment using 2 N hydrochloric acid at 37° C. for 1 hour, and BrdU positive cells were detected by using anti-BrdU antibody (Sigma) as a primary antibody, HRP-conjugated anti-mouse IgG antibody (Sigma) as a secondary antibody, and coloring with diaminobenzidine (DAB, Sigma). The ratio of BrdU positive cells to the total number of cells was calculated as the ratio of activated muscle satellite cells. The experiments were performed in 12 independent cell cultures in the case of the solvent control, and in 3 independent cultures in each concentration in the case of casuarinin or stachyurin. Data were expressed as the mean and standard deviation. The results are shown in Table 1 and FIGS. 1 and 2. The "*" in FIGS. 1 and 2 represents that the difference to the solvent control was statistically significant at p<0.05 by Dunnett's test.

TABLE 1

|  | Concentration | | Ratio of activated muscle satellite cells | | |
|---|---|---|---|---|---|
|  | µM | ng/mL | Mean | SD | p-value |
| Solvent control | — | — | 41.3% | 1.9% |  |
| Casuarinin | 0.01 | 13 | 43.3% | 5.7% |  |
|  | 0.03 | 25 | 44.9% | 0.8% |  |
|  | 0.05 | 50 | 51.3% | 1.9% | <0.05 |
|  | 0.1 | 100 | 50.8% | 4.3% | <0.05 |
|  | 0.3 | 250 | 48.8% | 0.4% | <0.05 |
|  | 1.1 | 1000 | 43.7% | 0.5% |  |
| Stachyurin | 0.09 | 83 | 44.7% | 6.1% |  |
|  | 0.4 | 333 | 48.5% | 3.1% | <0.05 |

Casuarinin and stachyurin showed a significant muscle satellite cell activating effect as the results demonstrated in Table 1 and FIGS. 1 and 2.

Comparative Example 1: Evaluation of Ratio of Activated Muscle Satellite Cells by Polyphenol Muscle satellite cell activating effects of polyphenols other than ellagitannins were evaluated similarly to Example 3 in order to determine whether or not the muscle satellite cell activating effect is specific to casuarinin and stachyurin. The used polyphenols other than ellagitannins were catechin (manufactured by Wako Pure Chemical Industries), myricitrin (manufactured by Adooq Bioscience), hyperin (manufactured by EXTRASYNTHESE) and quercitrin (manufactured by EXTRASYNTHESE). The concentration of each compound for the treatment was adjusted to 100 ng/mL. The result is shown in Table 2 and FIG. 3.

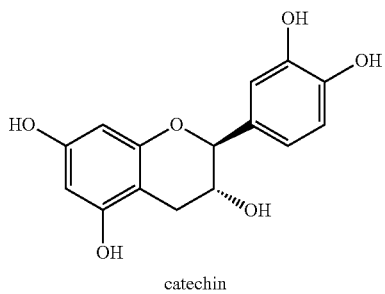

catechin

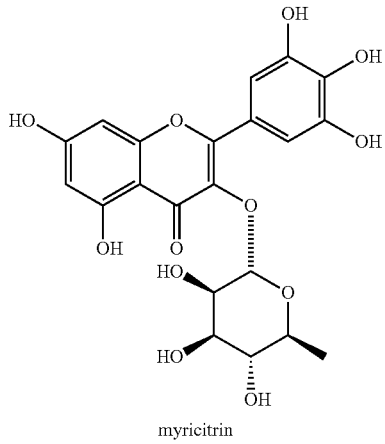

myricitrin

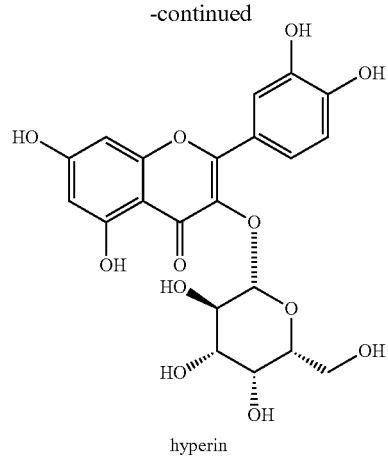

hyperin

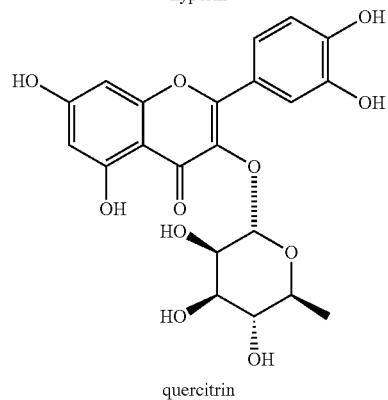

quercitrin

TABLE 2

|  | Concentration | | Ratio of activated muscle satellite cells | | |
|---|---|---|---|---|---|
|  | µM | ng/mL | Mean | SD | p-value |
| Solvent control | — | — | 41.3% | 1.9% |  |
| Catechin | 0.3 | 100 | 42.1% | 1.8% |  |
| Myricitrin | 0.2 | 100 | 41.8% | 3.0% |  |
| Hyperin | 0.2 | 100 | 38.2% | 4.2% |  |
| Quercitrin | 0.2 | 100 | 40.0% | 3.8% |  |

The above polyphenols other than ellagitannins did not show a clear muscle satellite cell activating effect in comparison with the solvent control as the results shown in Table 2 and FIG. 3.

Comparative Example 2: Evaluation of Ratio of Activated Muscle Satellite Cells by Other Ellagitannin and Partial Structure Muscle satellite cell activating effects were evaluated similarly to Example 3 in order to determine whether or not the other ellagitannins than casuarinin and stachyurin and partial structures have the muscle satellite cell activating effect similarly to casuarinin and stachyurin. The used other ellagitannin and partial structure were casuarictin manufactured by Nagara Science, castalagin manufactured by Sigma, gallic acid manufactured by Wako Pure Chemical Industries and ellagic acid manufactured by Wako Pure Chemical Industries. Casuarictin corresponds to casuarinin of which glucose part is closed. Castalagin corresponds to casuarinin in which 2,3-hexahydroxydiphenoyl group and 5-galloyl group are bound. Gallic acid corresponds to a partial structure of casuarinin and stachyurin. Casuarinin and stachyurin have hexahydroxydiphenoyl groups, and ellagic acid is formed by an intramolecular dehydration condensation of a hexahydroxydiphenoyl group. The concentration of each compound for the treatment was adjusted to 100 ng/mL. The result is shown in Table 3 and FIG. 4.

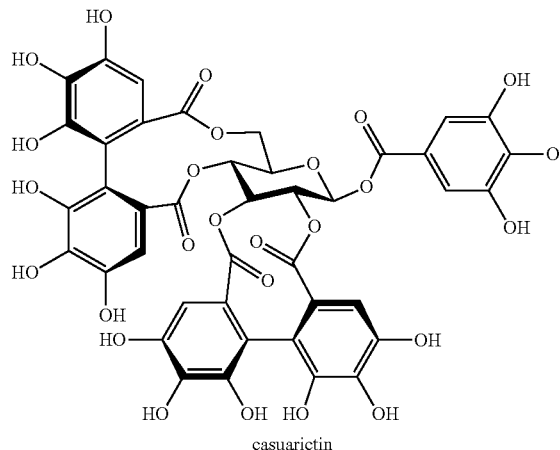

casuarictin

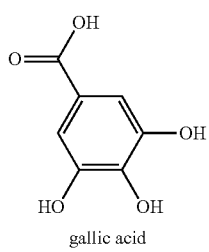

gallic acid

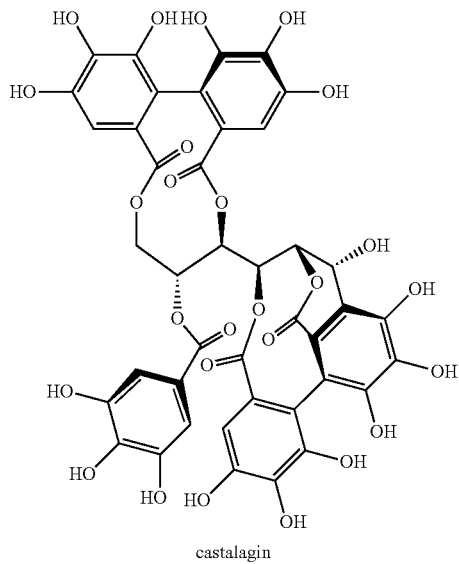

castalagin

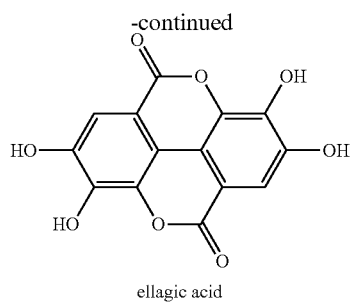

ellagic acid

TABLE 3

| | Concentration | | Ratio of activated muscle satellite cells | | |
|---|---|---|---|---|---|
| | μM | ng/mL | Mean | SD | p-value |
| Solvent control | — | — | 41.3% | 1.9% | |
| Casuarictin | 0.1 | 100 | 39.2% | 4.5% | |
| Castalagin | 0.1 | 100 | 39.4% | 1.4% | |
| Gallic acid | 0.6 | 100 | 37.8% | 2.7% | |
| Ellagic acid | 0.3 | 100 | 38.3% | 3.8% | |

The ellagitannin other than casuarinin and stachyurin, and the partial structure of casuarinin and stachyurin did not show a clear muscle satellite cell activating effect in comparison with the solvent control as the results shown in Table 3 and FIG. 4.

The above results clearly demonstrate that an excellent muscle satellite cell activating effect is specific to casuarinin and stachyurin.

The invention claimed is:

1. A method for relieving a condition due to a decline in muscle mass in a subject in need thereof, comprising
administering a preparation comprising a therapeutically effective amount of an ellagitannin compound represented by the following formula (I) as an active ingredient to the subject in need thereof:

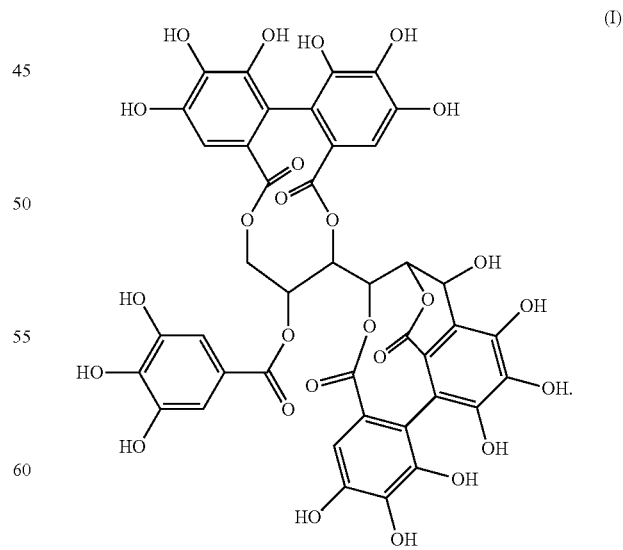

2. The method according to claim 1, wherein the ellagitannin compound represented by the formula (I) is casuarinin.

3. The method according to claim 1, wherein the ellagitannin compound represented by the formula (I) is stachyurin.

4. The method according to claim 1, wherein relieving the condition due to a decline in muscle mass comprises at least one of increasing muscle mass, maintaining muscle mass, increasing muscle force, maintaining muscle force, preventing a decrease of muscle mass, suppressing a decrease of muscle mass, preventing a decrease of muscle force, or suppressing a decrease of muscle force.

5. The method according to claim 1, wherein the subject is a human.

6. The method according to claim 1, wherein the subject is a human having one or more diseases selected from the group consisting of sarcopenia, locomotive syndrome and frailty.

7. The method according to claim 6, wherein the human is an elderly person.

8. The method according to claim 1, wherein 0.1 mg/kg weight/day or more of the ellagitannin compound represented by the formula (I) is administered.

9. The method according to claim 1, wherein the ellagitannin compound represented by the formula (I) is administered as a component of a food or drink composition.

10. The method according to claim 1, wherein the ellagitannin compound represented by the formula (I) is administered in an amount effective to activate a muscle satellite cell.

11. A method according to claim 1, wherein the preparation comprises a therapeutically effective amount for increasing muscle mass, maintaining muscle mass, increasing muscle force, maintaining muscle force, preventing a decrease of muscle mass, suppressing a decrease of muscle mass, preventing a decrease of muscle force, or suppressing a decrease of muscle force.

12. A method according to claim 1, wherein the preparation consists of a therapeutically effective amount of the ellagitannin compound represented by formula (I) as the active ingredient.

13. A method for increasing muscle mass in a subject in need thereof, comprising
administering a preparation comprising a therapeutically effective amount of an ellagitannin compound represented by the following formula (I) as an active ingredient to the subject in need thereof:

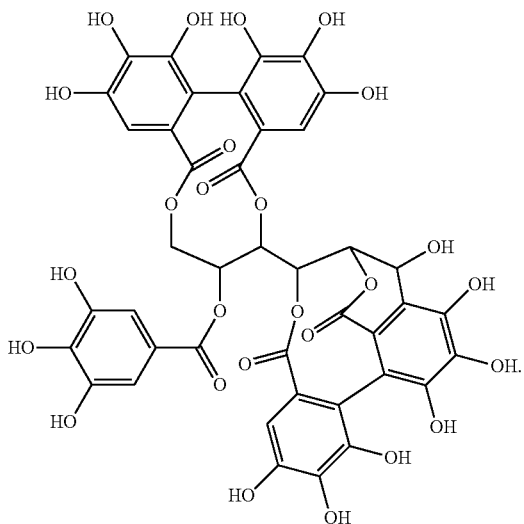

(I)

* * * * *